US00PP09317P

United States Patent [19]

Hanes

[11] Patent Number: Plant 9,317

[45] Date of Patent: Oct. 3, 1995

[54] GERANIUM NAMED 'AMERICANA WHITE SPLASH'

[75] Inventor: Mitchell E. Hanes, Morgan Hill, Calif.

[73] Assignee: Goldsmith Seeds, Inc., Gilroy, Calif.

[21] Appl. No.: 364,877

[22] Filed: Dec. 27, 1994

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Henderson & Sturm

[57] ABSTRACT

A new geranium cultivar particularly distinguished by green foliage, flowers that are white with a rose red spot, and semi-double in form on large umbels, fast rooting and a vigorous growth habit.

1 Drawing Sheet

BACKGROUND OF THE NEW PLANT

The present invention comprises a new and distinct cultivar of geranium, botanically known as *Pelargonium hortorum* Bailey, and hereinafter referred to by the cultivar name Americana White Splash. The new cultivar is propagated from a seedling resulting from the cross of a proprietary seed parent known as 3508-1 that has a blushing white flower with a rose colored spot pattern at the base of each petal. The seed parent was derived by crossing the variety Americana Light Pink (U.S. Plant Pat. No. 7,938) with an unpatented white flowered breeding line and thereafter selecting individual seedlings that had the white flower color and the basal petal spot pattern. The pollen parent used to make this hybrid is also a proprietary line, it is known as 3380-1. This plant is freely flowering, light lavender in color and it has the petal spot pattern, semi-double flower. This line was derived by crossing white flowered plants with pink flowered plants that also had the basal petal spot, and subsequently line crossing and selecting for near white flowers with the petal spot pattern.

Americana White Splash is a product of a planned breeding program intended to create new geranium cultivars with white colored flowers that have a basal petal spot pattern, semi-double flower form, green foliage, vigorous growth on a plant that is rounded in habit, freely flowering and with superior cutting productivity.

The new cultivar was created in 1993 in Gilroy, Calif. and has been repeatedly asexually reproduced by cuttings in Gilroy, Calif. and Guatemala over a 19 month period. It has also been trialed at Okemos, Mich. It has been found to retain its distinctive characteristics through successive propagations; and this novelty appears to be firmly fixed.

DESCRIPTION OF PHOTOGRAPH

This new geranium plant is illustrated by the accompanying photographs which show blooms, buds, and foliage of the plant in full color, the colors shown being as true as can be reasonably obtained by conventional photographic procedures.

DESCRIPTION OF THE NEW CULTIVAR

Figure 1:
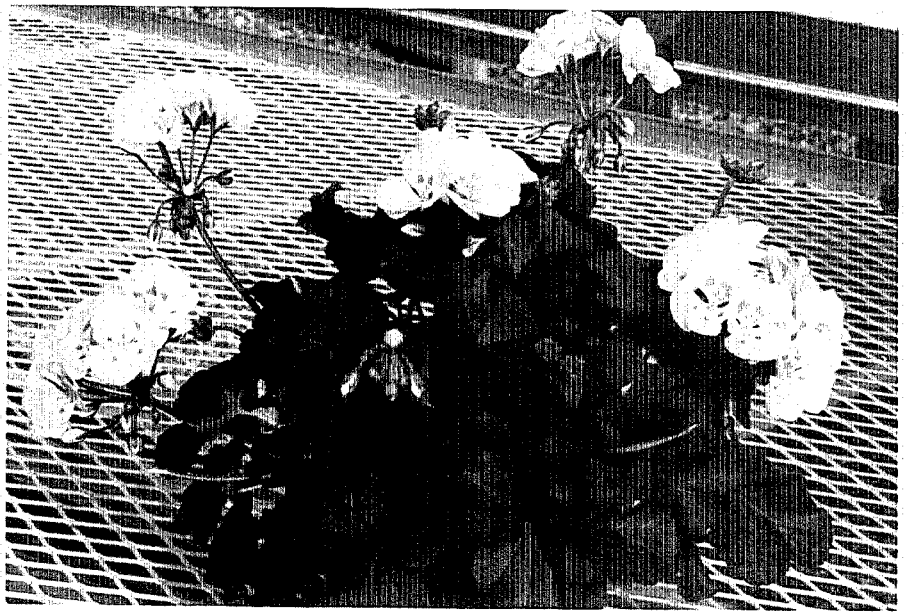
FIG. 1 shows overall plant habit.
Figure 2:
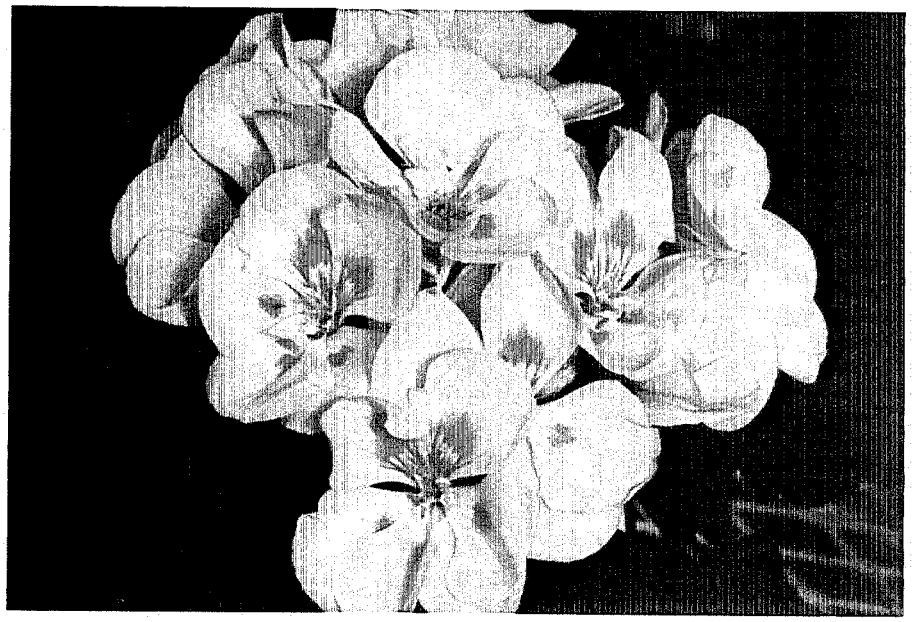
FIG. 2 illustrates the mature flower.

The following detailed descriptions set forth the distinctive characteristics of Americana White Splash. The data which defines these characteristics were collected from asexual reproductions carried out by Goldsmith Seeds, Inc.

in Gilroy, Calif. The plant history was taken on 12 week old plants, blossomed under natural light in a greenhouse and color readings were taken in the greenhouse (in Gilroy, Calif.) on Jun. 30, 1994 at 3:00 p.m. under ambient light. Color references are primarily to The R.H.S. Colour Chart of The Royal Horticultural Society of London (R.H.S.).

The Plant

Classification:

*Botanical.*—*Pelargonium hortorum* Bailey.

*Commercial.*—Zonal geranium.

Form: The plant has a rounded-mounded growth habit.

Height: 10 to 12 cm, as a 4 inch pot plant, excluding blooms.

Strength: Medium green foliage on a vigorous plant. Good shipping ability as rooted or unrooted cuttings.

Foliage: Abundant quantity.

*Leaves.*—Size: Diameter about 5–7 cm. Shape: Rounded cordate with occasional upfolding between veins. Margin: Irregularly crenate. Texture: Leathery and pubescent on both surfaces, especially along veins. Ribs and veins: Distinctly palmate, 2.5 to 4.0 cm long. Color: Upper side: Medium green. Under side: Lighter green color. Ribs and veins not prominently different from upper surface. Petioles: About 3.5 to 6.0 cm in length.

The Bud

Size:

*Diameter.*—About 5 mm.

Shape: Pointed ovoid.

Color: Petals when sepals first divide, 158C R.H.S.

Sepals: 5 in number, flat behind petals. Pointed linear lanceolate, R.H.S. 143C in an open flower.

The Flower

Blooming habit: Continuous, free flowering throughout the year.

Size: Approximately 4.5 cm in diameter, 1.0 cm deep, irregularly radially symmetrical.

Form: Cup-shaped when bloom first opens, later flattening to shallow cup shape with maturity.

Petals: 7 imbricate outer petals, 2.0–2.3 cm wide and approximately 2.1–2.6 cm long. Several inner smaller petaloids of varying shape. Both the outer petals and inner petaloids are white 155D R.H.S. The outer petals have the rose red spot pattern, 67C R.H.S. in the central region. The upper two petals have a feathered vein pattern up to the spot (same color). Color changing little with age. Underside of petals are white with the exception of the two upper petals which are white and show the feathered vein pattern Petals and petaloids soft and satiny.

Pedicel: Approximately 2.5–3.3 cm in length.

Persistence: Non-shattering flower.

Inflorescence

Type: An umbrel composed of approximately 27 flowers, erect or laterally ascending.

Peduncle: Approximately 11–15 cm in length, mostly 12 cm, green in color.

Reproductive Organs

Stamens:

*Anthers.*—8–9 positioned at or below the mature stigma, dull red prior to anthesis.

*Filaments.*—White near base and mid-length, graduating to dull red near anther.

*Pollen.*—Orange in color.

Pistil:

*Number.*—1.

*Length.*—Approximately 8 mm.

*Stigma.*—5 linear lobes of near equal length, curling back toward ovary, blush white in color.

*Style.*—Length: About 4–5 mm Color: Light green.

*Ovaries.*—At anthesis, densely pubescent with white hairs, oblong. Green drying to a light brown at maturity.

*Fruit.*—Partially fertile.

I claim:

1. A new and distinct cultivar of geranium substantially as herein shown and described, named Americana White Splash, that is characterized by: green foliage, flowers that are white with a rose red spot, and semi-double in form on large umbels, fast rooting and a vigorous growth habit.

* * * * *